United States Patent
Kobayashi (10) Patent No.: US 8,611,501 B2
(45) Date of Patent: Dec. 17, 2013

(54) X-RAY IMAGING APPARATUS

(75) Inventor: Kensuke Kobayashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/110,682

(22) Filed: May 18, 2011

(65) Prior Publication Data

US 2011/0222657 A1 Sep. 15, 2011

Related U.S. Application Data (63) Continuation of application No. PCT/JP2010/070504, filed on Nov. 17, 2010.

(30) Foreign Application Priority Data

Nov. 24, 2009 (JP) .................................. 2009-266493

(51) Int. Cl.
 *H05G 1/58* (2006.01)
(52) U.S. Cl.
 USPC ............................ 378/115; 378/98.8; 378/102
(58) Field of Classification Search
 USPC .................................. 378/98.8, 102, 114–116
 See application file for complete search history.

(56) References Cited

U.S. PATENT DOCUMENTS

| | | | |
|---|---|---|---|
| 7,239,685 B2 * | 7/2007 | Petrick et al. .................. 378/116 |
| 7,365,337 B2 * | 4/2008 | Tsuchino et al. ......... 250/370.09 |
| 7,426,261 B2 * | 9/2008 | Spahn ........................... 378/98.8 |
| 7,550,733 B2 * | 6/2009 | Endo et al. ............... 250/370.09 |
| 7,889,843 B2 * | 2/2011 | Watanabe ..................... 378/116 |
| 2007/0165783 A1* | 7/2007 | Abu Tabanjeh ............... 378/116 |

FOREIGN PATENT DOCUMENTS

| | | | |
|---|---|---|---|
| JP | 2005-208269 A | 8/2005 |
| JP | 2006-263322 A | 10/2006 |
| JP | 2009-183562 A | 8/2009 |
| JP | 2009-201968 A | 9/2009 |
| WO | 2006/080377 A | 8/2006 |
| WO | 2009/122808 A | 10/2009 |

* cited by examiner

*Primary Examiner* — Thomas R Artman
(74) *Attorney, Agent, or Firm* — Canon USA Inc. IP Division (57) ABSTRACT

An X-ray imaging apparatus includes an X-ray sensor configured to convert an X-ray into an image signal, a drive control unit configured to perform wireless communication with an external device and control driving of the X-ray sensor, a power supply unit configured to supply power to the X-ray sensor and the drive control unit, and a display unit configured to display information differently in accordance with one of the state of transmission and reception in the wireless communication and the remaining battery level state of the power supply unit and in accordance with the driving state of the X-ray sensor.

14 Claims, 12 Drawing Sheets

| CASE NO. | DRIVING STATE OF SENSOR | WIRELESS COMMUNICATION STATE | LED DISPLAY |
|---|---|---|---|
| 1 | POWER-OFF | COMMUNICATION NOT POSSIBLE | BLINKING BLUE LIGHT |
| 2 | POWER-OFF | COMMUNICATION POSSIBLE | LIGHT OFF |
| 3 | POWER-ON, BEFORE IMAGING PREPARATION | COMMUNICATION NOT POSSIBLE | BLINKING BLUE LIGHT |
| 4 | POWER-ON, BEFORE IMAGING PREPARATION | COMMUNICATION POSSIBLE | BLINKING GREEN LIGHT (MODE 1) |
| 5 | IMAGING PREPARATION IN PROGRESS | COMMUNICATION NOT POSSIBLE | BLINKING BLUE LIGHT |
| 6 | IMAGING PREPARATION IN PROGRESS | COMMUNICATION POSSIBLE | BLINKING GREEN LIGHT (MODE 2) |
| 7 | READY FOR IMAGING | COMMUNICATION NOT POSSIBLE | BLINKING BLUE LIGHT |
| 8 | READY FOR IMAGING | COMMUNICATION POSSIBLE | GREEN LIGHT ON |

FIG. 3A

FIG. 3B (DISPLAY EXAMPLE) ((( BAD )))

| CASE NO. | DRIVING STATE OF SENSOR | WIRELESS COMMUNICATION STATE | DISPLAYED CHARACTER |
|---|---|---|---|
| 1 | POWER-OFF | COMMUNICATION NOT POSSIBLE | BAD |
| 2 | POWER-OFF | COMMUNICATION POSSIBLE | SLEEP |
| 3 | POWER-ON, BEFORE IMAGING PREPARATION | COMMUNICATION NOT POSSIBLE | BAD |
| 4 | POWER-ON, BEFORE IMAGING PREPARATION | COMMUNICATION POSSIBLE | ACTIVE |
| 5 | IMAGING PREPARATION IN PROGRESS | COMMUNICATION NOT POSSIBLE | BAD |
| 6 | IMAGING PREPARATION IN PROGRESS | COMMUNICATION POSSIBLE | BLINKING "READY" |
| 7 | READY FOR IMAGING | COMMUNICATION NOT POSSIBLE | BAD |
| 8 | READY FOR IMAGING | COMMUNICATION POSSIBLE | READY |

FIG. 4A

FIG. 4B (DISPLAY EXAMPLE)

SENSOR  ◯ GREEN LIGHT ON

COM  ☼ BLINKING BLUE LIGHT

| CASE NO. | DRIVING STATE OF SENSOR | WIRELESS COMMUNICATION STATE | LED DISPLAY |
|---|---|---|---|
| 1 | POWER-OFF | COMMUNICATION NOT POSSIBLE | GREEN LIGHT OFF + BLINKING BLUE LIGHT |
| 2 | POWER-OFF | COMMUNICATION POSSIBLE | GREEN LIGHT OFF + BLUE LIGHT ON |
| 3 | POWER-ON, BEFORE IMAGING PREPARATION | COMMUNICATION NOT POSSIBLE | BLINKING GREEN LIGHT (MODE 1) + BLINKING BLUE LIGHT (MODE 2) |
| 4 | POWER-ON, BEFORE IMAGING PREPARATION | COMMUNICATION POSSIBLE | BLINKING GREEN LIGHT (MODE 1) + BLUE LIGHT ON |
| 5 | IMAGING PREPARATION IN PROGRESS | COMMUNICATION NOT POSSIBLE | BLINKING GREEN LIGHT (MODE 2) + BLINKING BLUE LIGHT (MODE 2) |
| 6 | IMAGING PREPARATION IN PROGRESS | COMMUNICATION POSSIBLE | BLINKING GREEN LIGHT (MODE 2) + BLUE LIGHT ON |
| 7 | READY FOR IMAGING | COMMUNICATION NOT POSSIBLE | GREEN LIGHT ON + BLINKING BLUE LIGHT (MODE 2) |
| 8 | READY FOR IMAGING | COMMUNICATION POSSIBLE | GREEN LIGHT ON + BLUE LIGHT ON |
| 9 | DRIVING ERROR | ARBITRARY STATE | BLINKING LIGHT OF ALL COLORS (MODE 2) |

FIG. 5

| | SENSOR | COM |
|---|---|---|
| (DISPLAY EXAMPLE) | READY | GOOD |

| CASE NO. | DRIVING STATE OF SENSOR | WIRELESS COMMUNICATION STATE |
|---|---|---|
| 1 | SLEEP | BAD |
| 2 | SLEEP | MIDDLE |
| 3 | SLEEP | GOOD |
| 4 | ACTIVE | BAD |
| 5 | ACTIVE | MIDDLE |
| 6 | ACTIVE | GOOD |
| 7 | READY | BAD |
| 8 | READY | MIDDLE |
| 9 | READY | GOOD |

FIG. 7B (DISPLAY EXAMPLE)

| | SENSOR | COM | BAT |
|---|---|---|---|
| | BLINKING GREEN LIGHT | BLINKING BLUE LIGHT | YELLOW LIGHT ON |

| CASE NO. | DRIVING STATE OF SENSOR | WIRELESS COMMUNICATION STATE | REMAINING BATTERY LEVEL OF BUILT-IN POWER SUPPLY UNIT | LED DISPLAY |
|---|---|---|---|---|
| 1 | ARBITRARY STATE | ARBITRARY STATE | NO REMAINING BATTERY LIFE | LIGHT OFF OF ALL COLORS |
| 2 | ARBITRARY STATE | COMMUNICATION POSSIBLE | NEARLY INSUFFICIENT REMAINING BATTERY LEVEL | GREEN LIGHT (OPTIONAL) + BLUE LIGHT ON + BLINKING YELLOW LIGHT |
| 3 | ARBITRARY STATE | COMMUNICATION NOT POSSIBLE | READY FOR IMAGING | BLINKING GREEN LIGHT(1) + BLINKING BLUE LIGHT + YELLOW LIGHT ON |
| 4 | POWER-OFF | COMMUNICATION POSSIBLE | READY FOR IMAGING | GREEN LIGHT OFF + BLUE LIGHT ON + YELLOW LIGHT ON |
| 5 | POWER-ON, BEFORE IMAGING PREPARATION | COMMUNICATION POSSIBLE | READY FOR IMAGING | BLINKING GREEN LIGHT(2) + BLUE LIGHT ON + YELLOW LIGHT ON |
| 6 | IMAGING PREPARATION IN PROGRESS | COMMUNICATION POSSIBLE | READY FOR IMAGING | BLINKING GREEN LIGHT(1) + BLUE LIGHT ON + YELLOW LIGHT ON |
| 7 | READY FOR IMAGING | COMMUNICATION POSSIBLE | READY FOR IMAGING | LIGHT ON OF ALL COLORS |
| 8 | DRIVING ERROR | COMMUNICATION POSSIBLE | READY FOR IMAGING | BLINKING LIGHT OF ALL COLORS (1) |

FIG. 8

(DISPLAY EXAMPLE)

| CASE NO. | SENSOR READY<br>DRIVING STATE OF SENSOR | COM GOOD<br>WIRELESS COMMUNICATION STATE | BAT OK<br>REMAINING BATTERY LEVEL OF BUILT-IN POWER |
|---|---|---|---|
| 1 | NON-DISPLAY | NON-DISPLAY | NON-DISPLAY (REMAINING BATTERY LEVEL OF ZERO) |
| 2 | ARBITRARY DISPLAY | GOOD | BLINKING "EMPTY" |
| 3 | ARBITRARY DISPLAY | BAD | OK |
| 4 | SLEEP | GOOD | OK |
| 5 | ACTIVE | GOOD | OK |
| 6 | BLINKING "READY" | GOOD | OK |
| 7 | READY | GOOD | OK |
| 8 | BLINKING "ERROR" | BLINKING "GOOD" | BLINKING "OK" |

X-RAY IMAGING APPARATUS

CROSS-REFERENCE TO RELATED APPLICATIONS

This application is a Continuation of International Patent Application No. PCT/JP2010/070504, filed Nov. 17, 2010, which claims the benefit of Japanese Patent Application No. 2009-266493, filed Nov. 24, 2009, both of which are hereby incorporated by reference herein in their entirety.

TECHNICAL FIELD

The present invention relates to an X-ray imaging apparatus including a wireless communication unit and a power supply unit.

BACKGROUND ART

X-ray photography in which an object is irradiated with X-rays and an intensity distribution of X-rays transmitted through the object is detected to obtain an X-ray image of the object has been widely used in the medical field and the industrial field. Methods for obtaining an X-ray image started with the film-screen method in which a light-sensitive film on which visible light emitted from a rare-earth phosphor sensitive to X-rays is incident undergoes chemical development to form a visible image. Since then, new methods have been developed through technological innovation. Among them, imaging apparatuses using a flat panel detector (FPD), which are based on semiconductor process technology, are available. The FPD is configured such that pixels each having a small photoelectric conversion element and a switching element are arranged in a grid pattern. Because of the significantly wider dynamic range than that of imaging apparatuses based on light-sensitive films of the related art, such imaging apparatuses have an advantage of the formation of stable X-ray images even if the amount of X-ray exposure changes. In addition, because of no need for chemical treatments, the imaging apparatuses also have an advantage of the immediate formation of X-ray images.

X-ray imaging apparatuses can be classified into the following types: a stationary type that is installed in a desired place such as in a standard radiography room, and a transportable type that can be freely moved. In recent years, the demand for transportable X-ray imaging apparatuses (hereinafter referred to as "electronic cassettes", or "cassettes" for short) has increased.

In the related art, an electronic cassette is electrically connected to a control unit via a cable used for feeding electric power from an external source and establishing communication with the control unit. Complicated cable wiring may cause a problem when an electronic cassette is used from place to place, and too long a cable may cause a situation where users may accidentally trip on the cable, leading to a possibility of the cable, the cassette, or the control unit being damaged.

In a clean (sterilized) environment such as in an operating room, furthermore, it is not desirable that a radiographic system including cables be in contact with an open (unsterilized) area such as the floor.

Recently, wireless cassettes configured to use a built-in power supply unit, instead of a cable, and adapted for wireless communication have emerged and are expected to markedly increase the flexibility of X-ray imaging. However, the stability of wireless communication is less than that of wired or cable connections which ensure physical connections, and the remaining battery level of the built-in power supply unit changes with time. Measures against these difficulties need to be taken.

The above problems have been addressed by Japanese Patent Laid-Open No. 2005-208269, Japanese Patent Laid-Open No. 2006-263322, and Japanese Patent Laid-Open No. 2009-201968, which disclose a drive control method to address an insufficient remaining battery level of a built-in power supply unit and a technology for displaying a state on an external control device.

However, in order to improve the imaging efficiency, it is important to quickly check the conditions of a cassette on the main body of the cassette. In an environment where a plurality of wireless cassettes are used under a single control device, it is desirable to immediately check which cassette the control device is communicating with or whether or not the X-ray sensor of the cassette that the control device is communicating with is correctly operating.

It is also desirable to take measures against less stability of wireless communication than that of wired connections which ensure physical connections and against the changes in the remaining battery level of the built-in power supply unit over time.

CITATION LIST

Patent Literature

PTL 1 Japanese Patent Laid-Open No. 2005-208269
PTL 2 Japanese Patent Laid-Open No. 2006-263322
PTL 3 Japanese Patent Laid-Open No. 2009-201968

SUMMARY OF INVENTION

The present invention provides an X-ray imaging apparatus that overcomes at least one of the above difficulties.

Accordingly, an X-ray imaging apparatus according to the present invention includes an X-ray sensor configured to convert an X-ray into an image signal, a drive control unit configured to perform wireless communication with an external device and control driving of the X-ray sensor, and a display unit configured to display a sign differently in accordance with the driving state of the X-ray sensor and the state of transmission and reception in the wireless communication.

Further features of the present invention will become apparent from the following description of exemplary embodiments with reference to the attached drawings.

DESCRIPTION OF EMBODIMENTS

Embodiments of the present invention will be described in detail hereinafter with reference to the drawings.

First Embodiment

Figure 1:
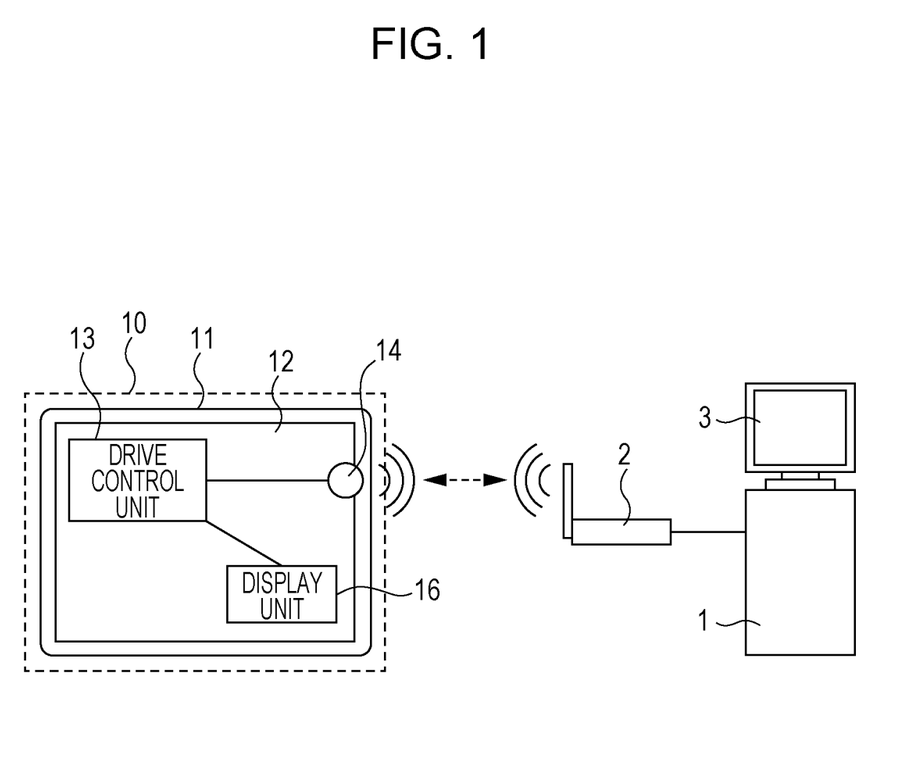
FIG. 1 is a schematic view of an X-ray imaging apparatus.

FIG. 1 schematically illustrates an X-ray imaging apparatus according to first to fourth embodiments. A cassette 10 performs wireless communication with an external device 1 by operating an antenna 14, and has a housing 11 including an X-ray sensor 12 and a drive control unit 13. The housing 11 also includes a display unit 16 formed of a light-emitting diode (LED) light that is a display light source. The display unit 16 displays information that is changed in accordance with the state of the X-ray sensor 12 and the wireless communication state. The X-ray sensor 12 converts an X-ray into an image signal. The X-ray sensor 12 has, for example, the following four normal driving states: (1) a power-off state (or "sleep state"), (2) a power-on and stand-by state of waiting for a signal from the drive control unit 13 ("before imaging preparation"), (3) a state where a transition to a state of getting ready for imaging (hereinafter referred to as a "ready-for-imaging state") is in progress ("imaging preparation in progress"), and (4) the ready-for-imaging state. The drive control unit 13 causes the display unit 16 to display the detected states, i.e., the driving state of the X-ray sensor 12 and the state of transmission and reception in wireless communication.

Figure 2A:
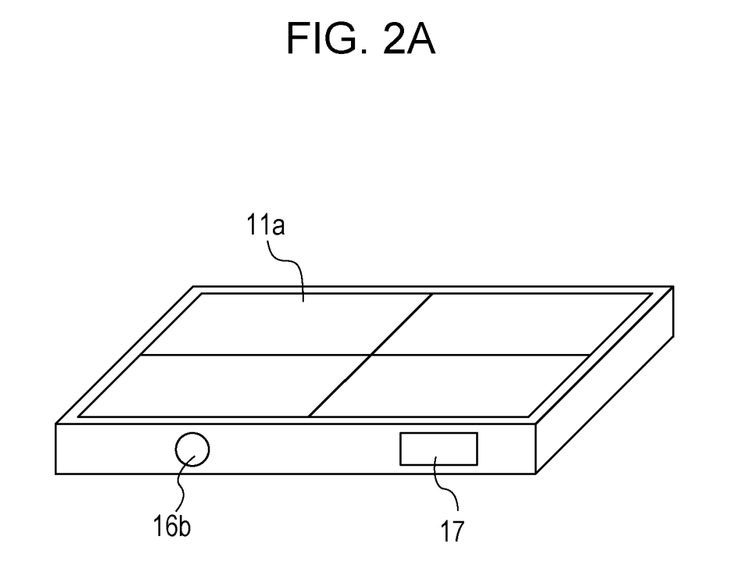
FIGS. 2A and 2B illustrate the X-ray imaging apparatus.

FIG. 2A illustrates an example of elements mounted in the housing 11. An LED light 16b for displaying a state and an antenna opening 17 are arranged side by side on a surface different from a surface 11a irradiated with X-rays. Because of the characteristics of radio waves, it is not desirable that an object which could be an obstacle be arranged near the antenna opening 17. It is also necessary to remove any object that obstructs the user's vision near the display unit 16. In this embodiment, since such elements suffering constraints are collectively located in the same surface, the number of surfaces including such constrained elements can be minimized. The shape of the LED light 16b is not limited to that illustrated in FIG. 2A.

Figure 2B:
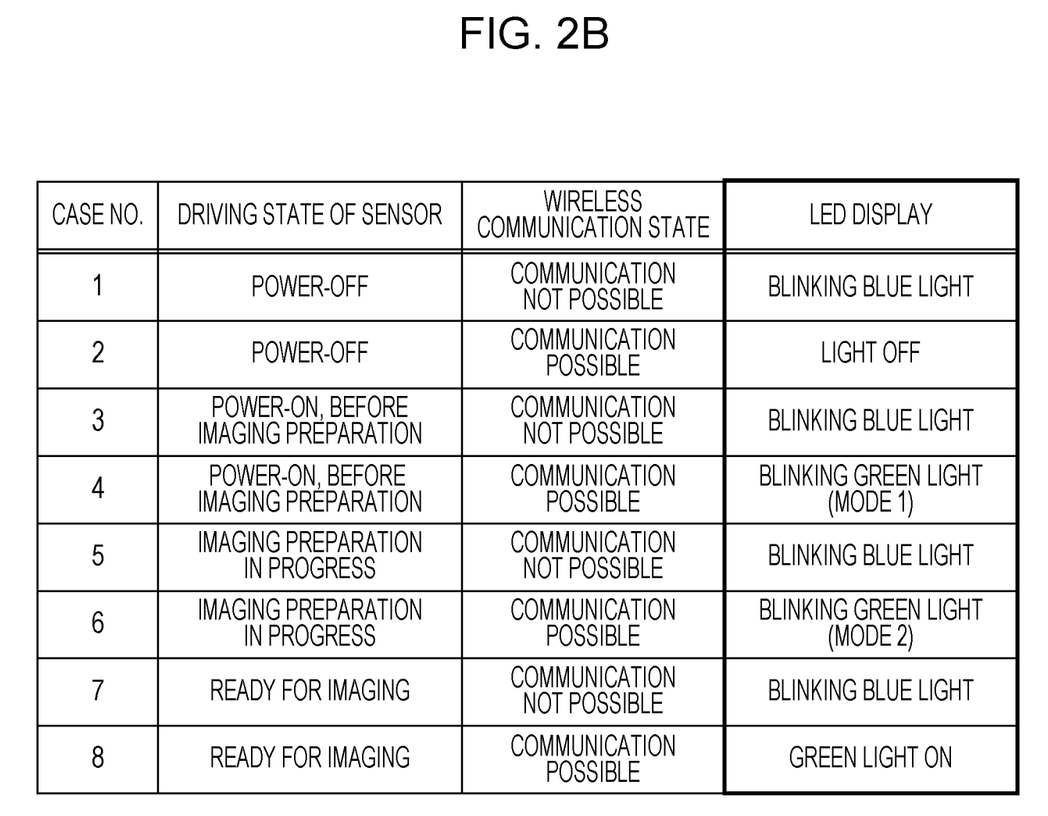

The LED light 16b is turned on and off and blinks using patterns illustrated in FIG. 2B. In a state where wireless communication is possible, the driving state of the X-ray sensor 12 is indicated using green light. Referring to FIG. 2B, in mode 1 and mode 2, the green LED light blinks at different speeds ("blinking speeds") which are visually distinguishable. If wireless communication is not possible, the drive control unit 13 is not allowed to receive a signal for changing the driving state of the X-ray sensor 12. Users are informed that the wireless communication is not possible with blinking blue light regardless of the driving state of the X-ray sensor 12. According to this embodiment, users can easily determine whether they can perform the imaging operation. The colors of the LED light 16b may be any two colors other than those described above as long as two visually distinguishable colors are used.

The drive control unit 13 controls the driving state of the X-ray sensor 12 in accordance with the wireless communication state. For example, if the X-ray sensor 12 is in the ready-for-imaging state (state (4)), the drive control unit 13 causes a transition to either the power-off state (sleep state) (state (1)) or the power-on and stand-by state of waiting for a signal from the drive control unit 13 (before imaging preparation) (state (2)). Furthermore, in accordance with the standard of the wireless communication state during a predetermined period of time, the drive control unit 13 causes a transition to either the power-off state (sleep state) (state (1)) or the power-on and stand-by state of waiting for a signal from the drive control unit 13 (before imaging preparation) (state (2)). In this case, if the communication state is bad, the power supply to the X-ray sensor 12 is stopped, and the X-ray sensor 12 enters the state (1), thereby preventing the unnecessary generation of heat or the occurrence of dark currents. If the recovery of the communication state is expected, the drive control unit 13 causes the X-ray sensor 12 to stand by in the state (2), thereby preventing users from missing opportunities to obtain desired images. Here, the display unit 16 displays information differently when the driving state of the X-ray sensor 12 has been changed in accordance with the wireless communication state and when the driving state of the X-ray sensor 12 has been changed otherwise. For example, the color of the LED light indicating the driving state of the X-ray sensor 12 is changed. Thus, users can determine whether the driving state of the X-ray sensor 12 has been changed in accordance with the wireless communication state or by using a standard process.

Second Embodiment

Figure 3A:
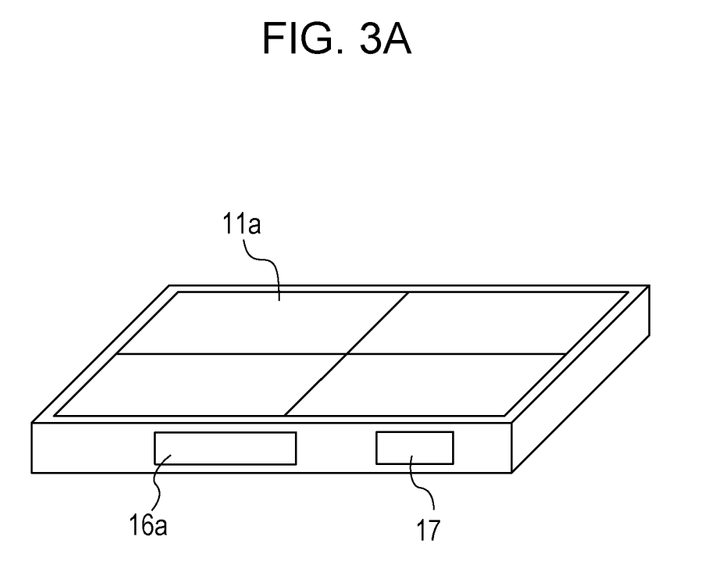
FIGS. 3A and 3B illustrate an X-ray imaging apparatus.

FIG. 3A illustrates an example of elements mounted in the housing 11 according to this embodiment. A liquid crystal display 16a for displaying a state and an antenna opening 17 are arranged side by side on a surface different from a surface 11a irradiated with X-rays. Thus, advantages similar to those in the first embodiment are achieved. The liquid crystal display 16a may be replaced by another display having equivalent functionality, such as an organic electroluminescent (EL) display.

Figure 3B:
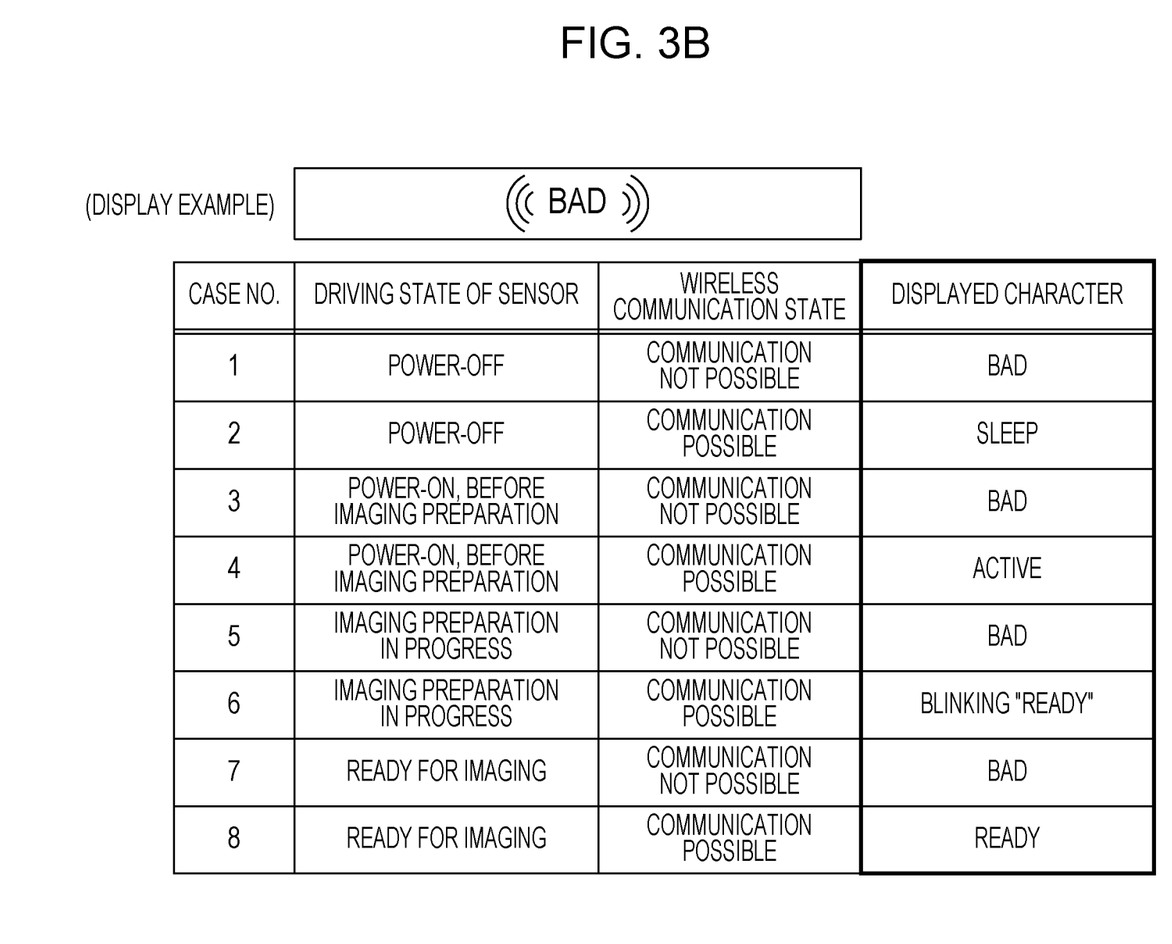

FIG. 3B illustrates an example of display patterns on the liquid crystal display 16a. If wireless communication is possible, signs ("SLEEP"/"ACTIVE"/blinking "READY"/ "READY") are displayed to indicate only the driving state of the X-ray sensor 12. If wireless communication is not possible, as illustrated in the display example, "BAD" is displayed regardless of the driving state of the X-ray sensor 12. This embodiment allows recognition of signs having different appearances such as characters, and provides more visibility than the first embodiment in which only colors and lighting conditions are used as signs. The characters may be replaced by other signs having different appearances such as picture icons.

Third Embodiment

Figure 4A:
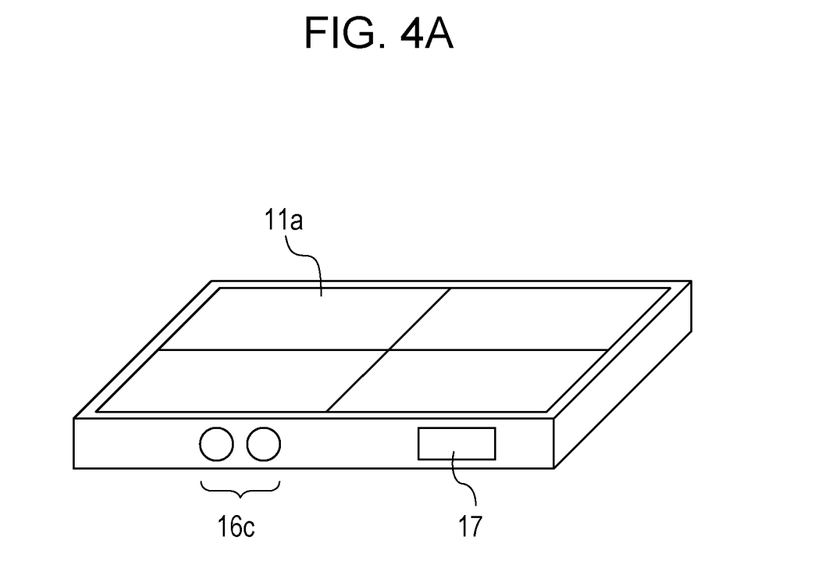
FIGS. 4A and 4B illustrate an X-ray imaging apparatus.
Figure 4B:
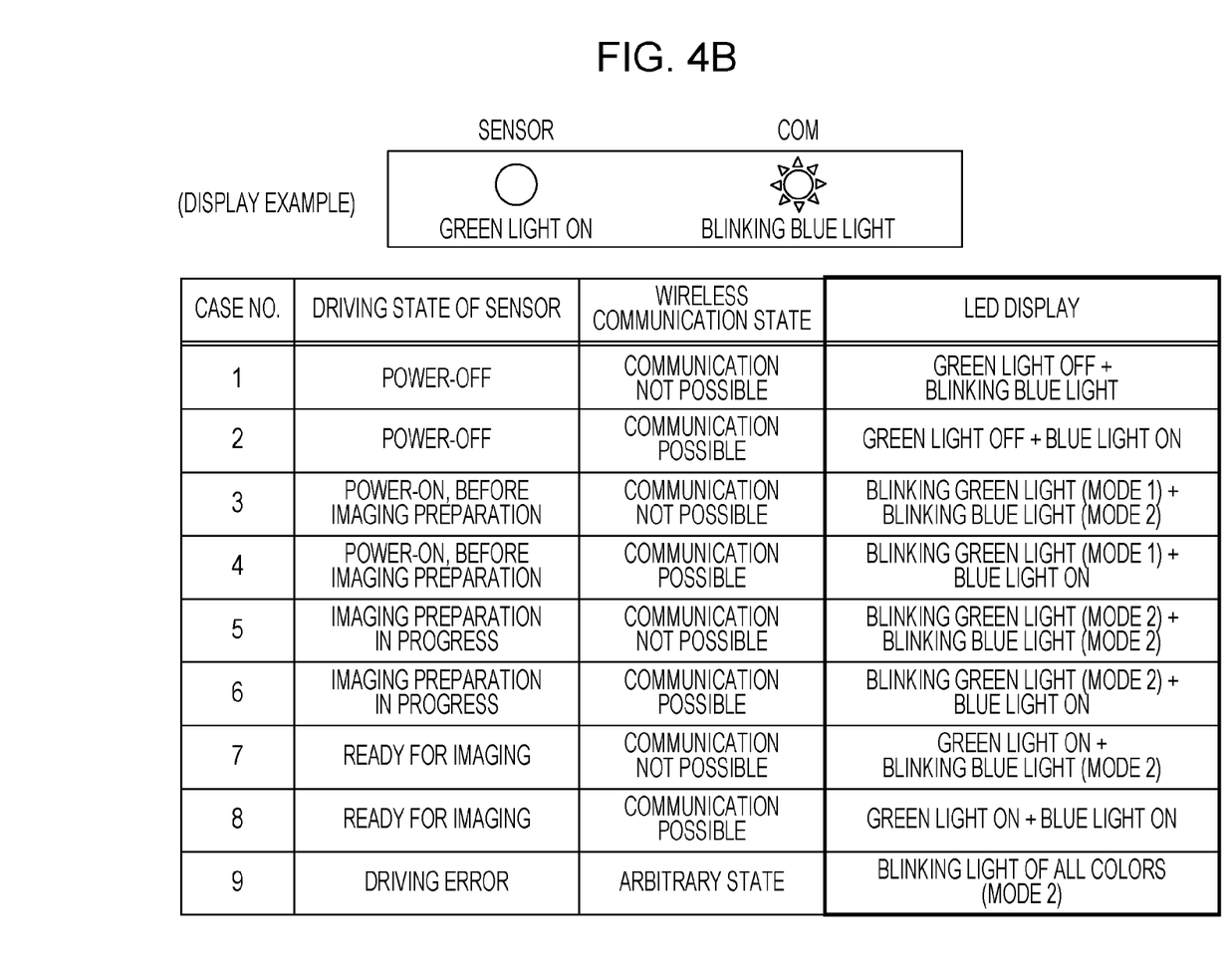

In this embodiment, referring to FIG. 4A, LED lights 16C including a green LED light and a blue LED light are mounted. By way of example, the green LED light indicates the driving state of the X-ray sensor 12 and the blue LED light indicates the wireless communication state. The display of the LED lights is changed using patterns illustrated in FIG. 4B. Here, the green LED light blinks in mode 1 and mode 2 representing different blinking speeds which are visually distinguishable. The display example in FIG. 4B illustrates a state where wireless communication is not possible although the X-ray sensor 12 is ready for imaging. In this manner, users can recognize the driving state of the X-ray sensor 12 independently of the wireless communication state, and can understand the reason why they are not allowed to perform an imaging operation on the basis of the two states simultaneously, namely, the wireless communication state and the driving state of the X-ray sensor 12. In addition, users can also be informed of any driving error of the X-ray sensor 12. As illustrated in the display example, LED lights may be provided together with signs to describe what is indicated by the LED lights ("SENSOR" means the driving state of the X-ray sensor 12 and "COM" means the wireless communication state) to help users recognize the respective states. The colors of the LED lights may be any two colors other than those described above as long as two colors visually distinguishable are used. Accordingly, a combination of lighting patterns of a plurality of LED lights allows users to easily identify the cause of non-permission of imaging. The plurality of LED lights may be a predetermined number of LED lights.

Fourth Embodiment

Figure 5:
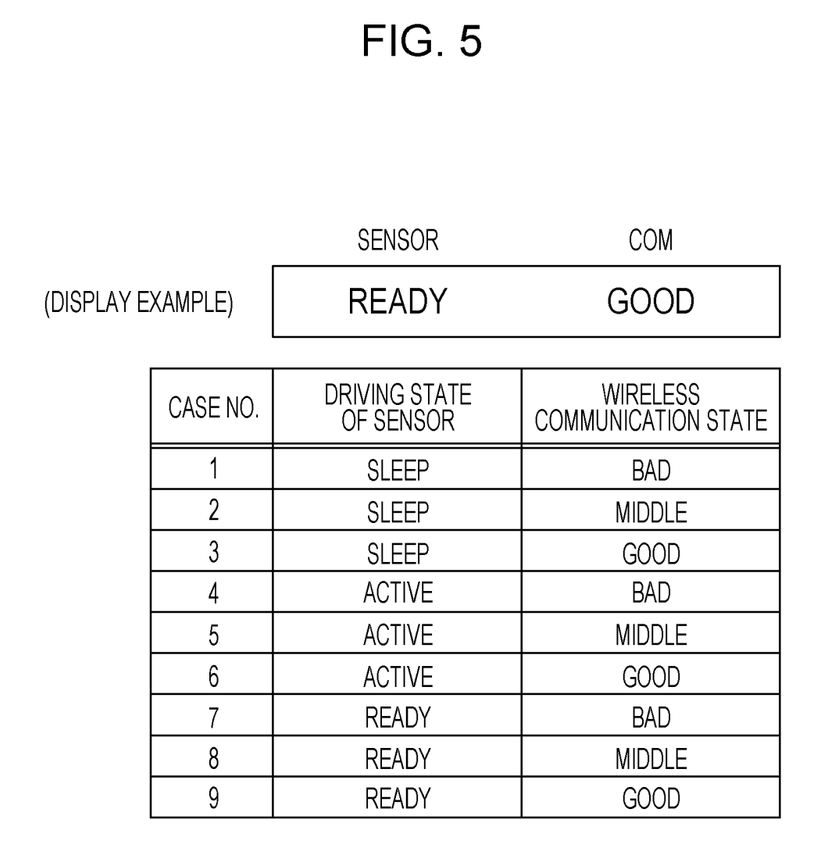
FIG. 5 illustrates changing patterns of displayed states.

This embodiment has a feature in that with the elements mounted in the manner illustrated in FIG. 3A, the information displayed on the liquid crystal display 16a is changed as illustrated in FIG. 5. With regard to the driving state of the X-ray sensor 12, "SLEEP" is displayed when the X-ray sensor 12 is in the power-off state, "ACTIVE" is displayed when the X-ray sensor 12 has not yet started imaging preparation, blinking "READY" is displayed when the X-ray sensor 12 is performing imaging preparation, "READY" is displayed when the X-ray sensor 12 is in the ready-for-imaging state, and "ERROR" is displayed if a driving error has occurred (regardless of the wireless communication state). With regard to the wireless communication state, "GOOD" is displayed if the state of transmission and reception is good, "BAD" is displayed if transmission or reception is not possible, and "MIDDLE" indicating a level between the two states is displayed. The display example illustrated in FIG. 5 illustrates that the X-ray sensor 12 is ready for imaging and the wireless communication state is good. This embodiment has advantages of providing high visibility using characters, which allow users to understand a state at a glance, and providing a detailed understanding of the wireless communication state based on radio field intensity. To indicate whether wireless communication is possible or not, it is not necessary to display "MIDDLE".

Fifth Embodiment

Figure 6:
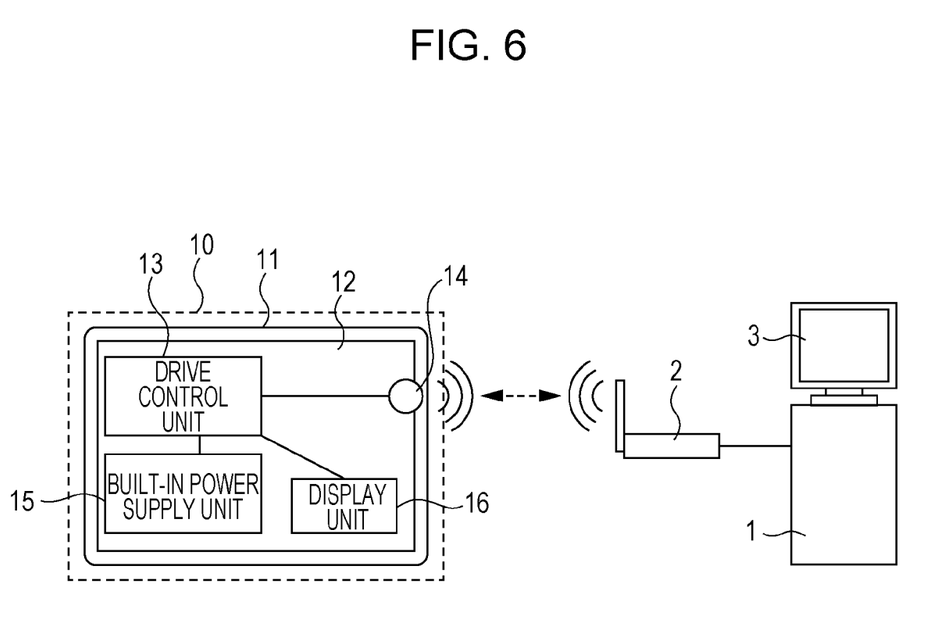
FIG. 6 is a schematic view of an X-ray imaging apparatus.

FIG. 6 schematically illustrates an X-ray imaging apparatus according to fifth and sixth embodiments in which a built-in power supply unit 15 and the function for displaying the state of the built-in power supply unit 15 are added to the X-ray imaging apparatus (electronic cassette) 10 illustrated in FIG. 1. The built-in power supply unit 15 supplies electric power to the X-ray sensor 12 and the drive control unit 13. Thus, the external device 1 can be informed of the states of main elements of a wireless electronic cassette, that is, the state of the X-ray sensor 12, the wireless communication state, and the remaining battery level of the built-in power supply unit 15.

Figure 7A:
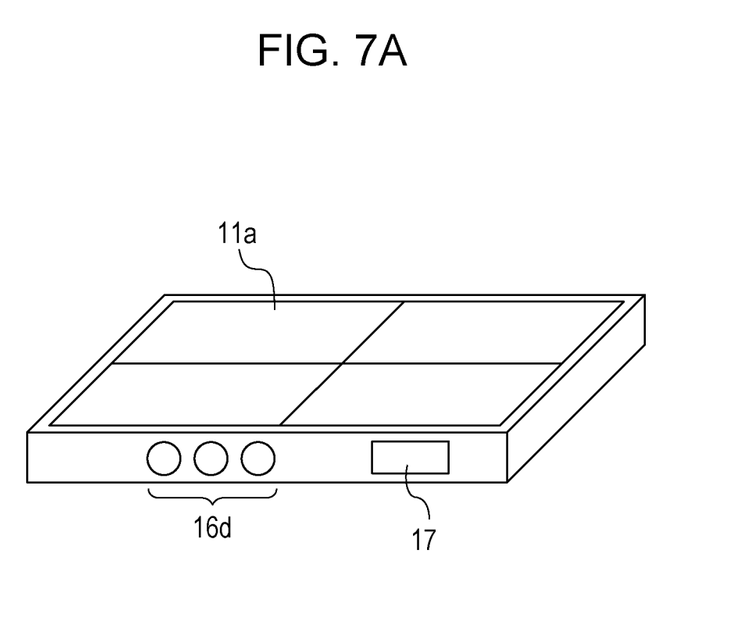
FIGS. 7A and 7B illustrate an X-ray imaging apparatus.
Figure 7B:
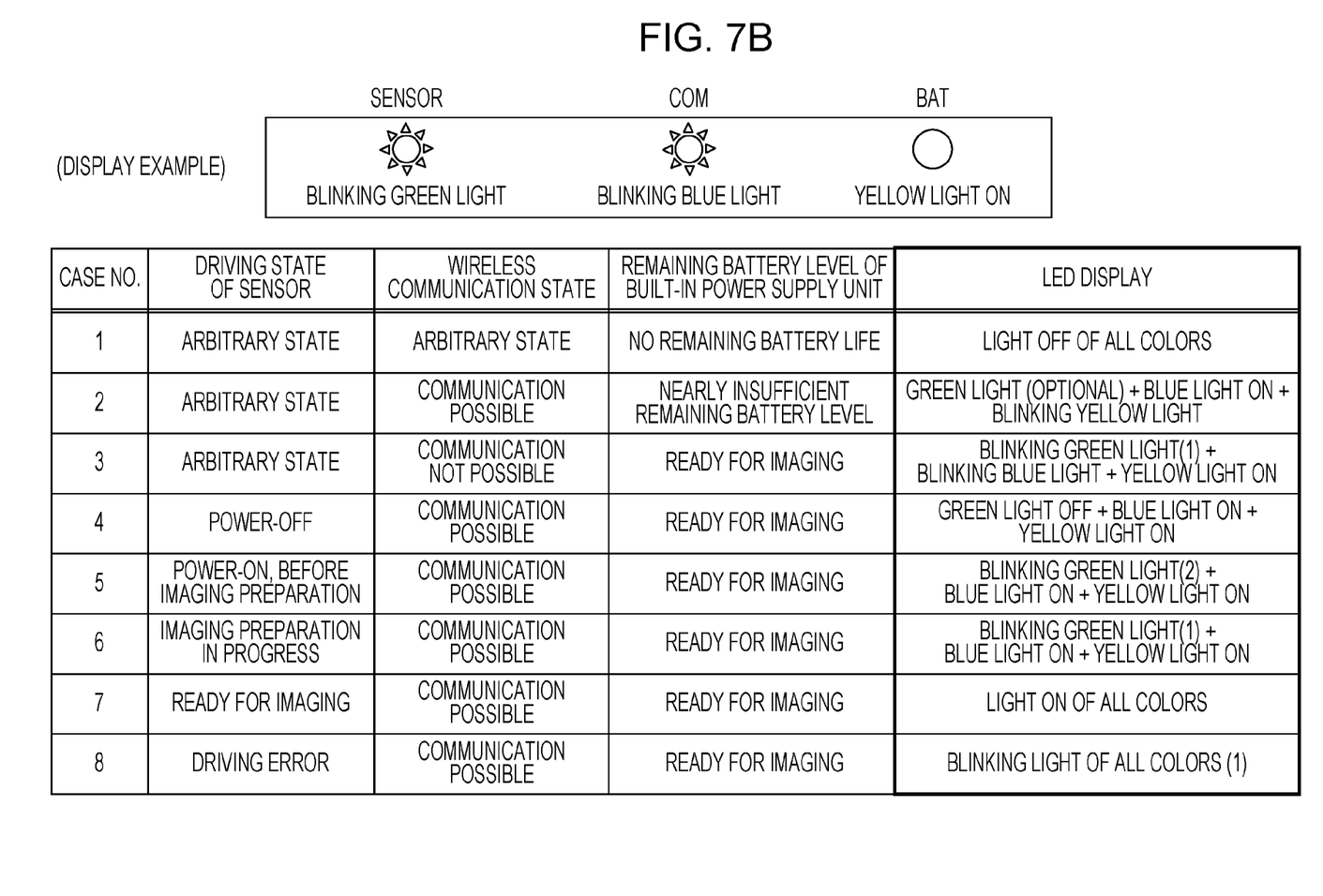

FIG. 7A illustrates an example of elements mounted in the housing 11. LED lights 16d for displaying the states of the above three elements and an antenna opening 17 are arranged side by side on a surface different from a surface 11a irradiated with X-rays, and it is desirable that no object be placed near the surface 11a. Advantageously, other installation constraints are not taken into account. The display of the LED lights 16d is changed using patterns illustrated in FIG. 7B in accordance with the states of the respective elements. Here, numbers 1 and 2 in parentheses that follow blinking LED lights denote the mode numbers representing the blinking speeds, and the blinking speeds are different to the extent that they are visually distinguishable. LED lights of all the colors blink in mode 2 only when a driving error occurs in the X-ray sensor 12. If the remaining battery level of the built-in power supply unit 15 is reduced to the level that does not maintain the functionality of the electronic cassette 10 (no remaining battery life), all the LED lights are turned off and the power supply to the X-ray sensor 12 is also stopped. In FIG. 7B, the term "insufficient remaining battery level" refers to a state where the remaining battery level of the built-in power supply unit 15 is below the remaining battery level necessary to process the most immediate imaging order among imaging orders held in either of or both the external device 1 and the drive control unit 13. This invites users to charge the built-in power supply unit 15, and prohibits them from performing further imaging operations, thereby preventing unwanted interruption of imaging. As illustrated in the display example illustrated in FIG. 7B, furthermore, if wireless communication is not possible even though the built-in power supply unit 15 has a sufficient remaining battery level and the X-ray sensor 12 is correctly operating, users are caused to stop their imaging operation, and are informed that they are not allowed to perform an imaging operation. This control can prevent in advance the occurrence of unwanted radiation of X-rays caused by lost of image data. In this case, for example, if the state of the X-ray sensor 12, the wireless communication state, or the state of the built-in power supply unit 15 is detected to be abnormal, users are caused to stop the imaging operation to make control and the display pattern simple. In addition, a plurality of LED lights blink. Thus, users can easily recognize the abnormal condition. "SENSOR", "COM", and "BAT" are displayed in the vicinity of the LED lights 16d, representing the driving state of the X-ray sensor 12, the wireless communication state, and the remaining battery level of the built-in power supply unit 15, respectively. The colors of the LED lights may be any three colors other than those described above as long as three visually distinguishable colors are used.

Furthermore, the remaining battery level of the built-in power supply unit 15 may be displayed not in a binary manner as described above but by level-based indication in which plurality of LED lights are turned on in accordance with three or more remaining battery levels.

Sixth Embodiment

Figure 8:
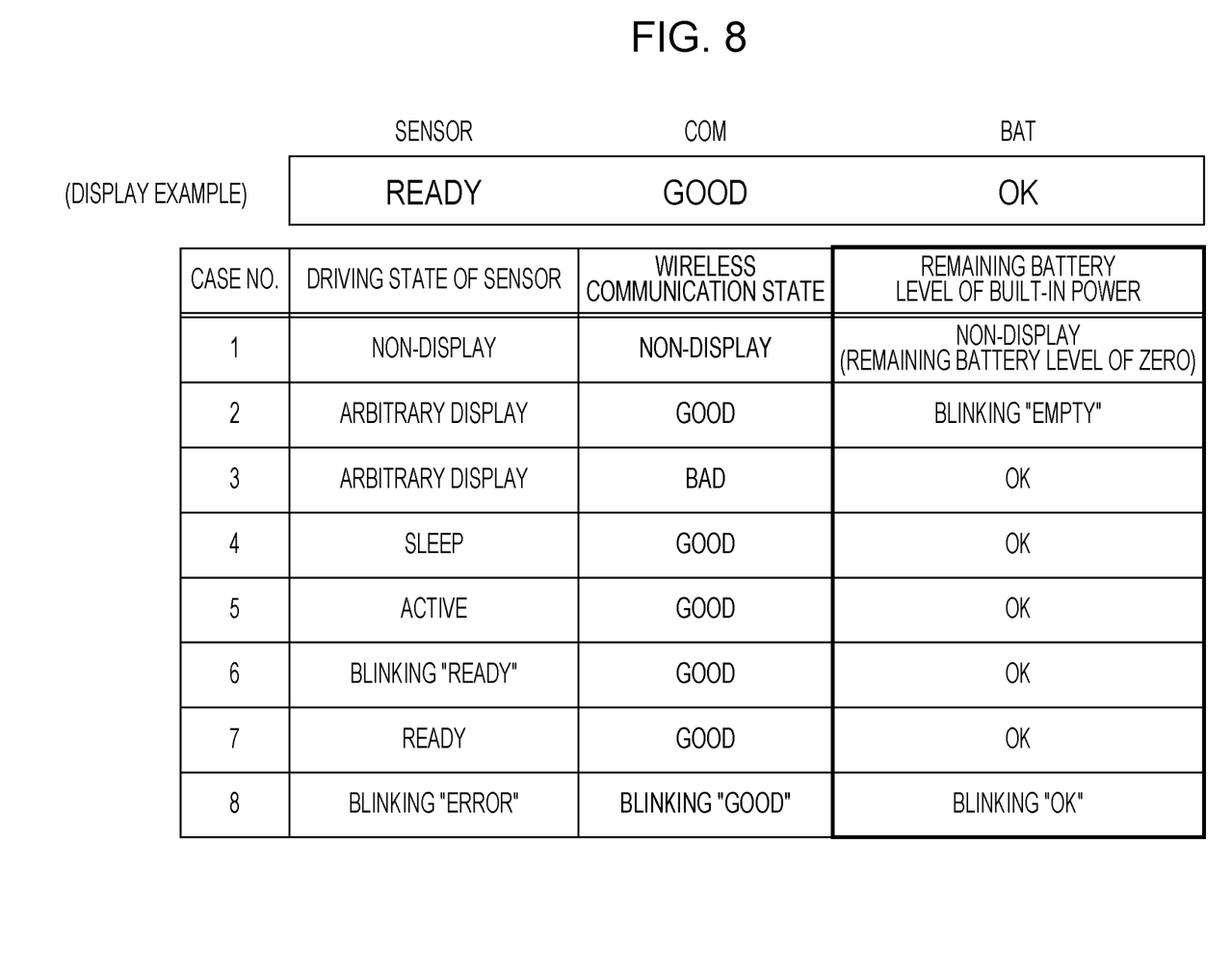
FIG. 8 illustrates changing patterns of displayed states.

In this embodiment, in the electronic cassette 10 having elements mounted in the manner illustrated in FIG. 3A, the display of the liquid crystal display 16a is changed as illustrated in FIG. 8. In FIG. 8, the case numbers correspond to those in the display patterns according to the fifth embodiment described above (FIG. 7B). That is, with regard to the driving state of the X-ray sensor 12, "SLEEP" is displayed when the X-ray sensor 12 is in the power-off state (sleep state), "ACTIVE" is displayed when the X-ray sensor 12 is in the power-on state but has not yet started imaging preparation, "READY" (blinking) is displayed when the X-ray sensor 12 is in the imaging-in-preparation state, and "READY" (blinking) is displayed when the X-ray sensor 12 is in the ready-for-imaging state. With regard to the wireless communication state, "GOOD" is displayed if transmission and reception are allowed, and "BAD" is displayed if transmission or reception is not possible. Furthermore, with regard to the remaining battery level of the built-in power supply unit 15, "OK" is displayed if the built-in power supply unit 15 has a sufficient remaining battery level to continue the imaging operation, and blinking "EMPTY" is displayed if the remaining battery level is below the remaining battery level necessary to process the most immediate imaging order among imaging orders held in either of or both the external device 1 and the drive control unit 13. The display example in FIG. 8 illustrates Case No. 7 in which the X-ray sensor 12 is in the ready-for-imaging state, the wireless communication is good, and the built-in power supply unit 15 has a sufficient remaining battery level to continue the imaging operation. For Case No. 8 in which a driving error is found in the X-ray sensor 12, all the indicators are made to blink to attract users' attention. This embodiment has an advantage of providing higher visibility using characters which are changed than the fifth embodiment in which colors and blinking speeds are used as signs.

A remaining battery level necessary to process all the imaging orders held in either of or both the external device 1 and the drive control unit 13 may be added to a remaining battery level threshold for changing the display of the remaining battery level of the built-in power supply unit 15 to thereby change the display. Accordingly, before executing successive imaging orders, users can turn in advance their attention to the remaining battery level of the built-in power supply unit 15 that will become insufficient during the execution of the imaging orders.

It is to be understood that the present invention is not to be limited to the foregoing embodiments, and various changes and modifications may be made without departing from the spirit and scope of the present invention. Therefore, the appended claims are attached in order to clearly define the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An X-ray imaging apparatus comprising:
an X-ray sensor configured to convert an X-ray into an image signal;
a drive control unit configured to perform wireless communication with an external device and control driving of the X-ray sensor;
a power supply unit configured to supply power to the X-ray sensor and the drive control unit; and
a display unit configured to display information that is changed in accordance with one of a state of transmission and reception in the wireless communication and a remaining battery level of the power supply unit and in accordance with a driving state of the X-ray sensor,
wherein the drive control unit is configured to control the X-ray sensor to transition from a first state of power consumption to a second state of power consumption lower than the first state, in response to a change in a wireless communication state during a predetermined period of time, and
wherein, when the wireless communication state changes to an state where communication is not possible during the predetermined period of time, the drive control unit is not allowed to change a driving state of the X-ray sensor.

2. The X-ray imaging apparatus according to claim 1, wherein the drive control unit controls the driving state of the X-ray sensor in accordance with a communication state, and
wherein the display unit displays the information differently when the driving state of the X-ray sensor has been changed in accordance with the communication state and when the driving state of the X-ray sensor has been changed in accordance with a state other than the communication state.

3. The X-ray imaging apparatus according to claim 1, wherein the drive control unit controls the driving state of the X-ray sensor so that in a case that communication with the external device is not possible, the driving state of the X-ray sensor enters a sleep state where the X-ray sensor is powered off, and
wherein the drive control unit controls the driving state of the X-ray sensor so that when recovery of the communication state is expected, the driving state of the X-ray sensor enters a state where the X-ray sensor is powered on and is to start imaging preparation.

4. The X-ray imaging apparatus according to claim 1, wherein the display unit includes a plurality of light-emitting diode lights, and displays information in accordance with the driving state of the X-ray sensor and the state of transmission and reception in the wireless communication by using a combination of lighting patterns of the plurality of LED lights.

5. The X-ray imaging apparatus according to claim 1, wherein the X-ray imaging apparatus has a housing including the X-ray sensor, and the housing has a surface on which an antenna operating in the wireless communication and the display unit are provided.

6. The X-ray imaging apparatus according to claim 1, wherein the display unit displays whether or not the X-ray sensor is ready for imaging, and also displays whether or not the wireless communication is possible.

7. The X-ray imaging apparatus according to claim 1, wherein the power supply unit is configured to supply power for driving the X-ray sensor and the drive control unit, and
wherein the display unit displays a remaining battery level of the power supply unit.

8. The X-ray imaging apparatus according to claim 1, wherein the display unit changes the displayed information when a remaining battery level of the power supply unit is below a certain level.

9. The X-ray imaging apparatus according to claim 1, wherein the display unit includes a certain number of light sources.

10. The X-ray imaging apparatus according to claim 1, wherein the display unit includes a plurality of display devices.

11. The X-ray imaging apparatus according to claim 1, wherein the display unit is one of a display configured to display a character or a picture icon and a light-emitting diode light.

12. The X-ray imaging apparatus according to claim 9, wherein the display unit includes a first light emitting diode (LED) configured to indicate the driving state of the X-ray sensor, a second LED configured to indicate a wireless communication state, and a third LED configured to indicate a remaining battery level of the power supply unit.

13. The X-ray imaging apparatus according to claim 1, wherein, when the wireless communication state changes to the state where communication is not possible during the predetermined period of time, the power supply to the X-ray sensor is stopped.

14. The X-ray imaging apparatus according to claim 1, wherein, when the wireless communication state changes to the state where communication is not possible during the predetermined period of time, the display unit displays the state of wireless communication.

* * * * *